(12) United States Patent
Yamaguchi et al.

(10) Patent No.: US 6,184,983 B1
(45) Date of Patent: Feb. 6, 2001

(54) METHOD AND APPARATUS FOR MEASURING TURBIDITY

(75) Inventors: Dabide Yamaguchi; Tokio Ohto, both of Kanagawa; Kenji Harada; Akinori Sasaki, both of Tokyo, all of (JP)

(73) Assignee: Fuji Electric Co., Ltd., Kanagawa (JP)

( * ) Notice: Under 35 U.S.C. 154(b), the term of this patent shall be extended for 0 days.

(21) Appl. No.: 09/037,431

(22) Filed: Mar. 10, 1998

(30) Foreign Application Priority Data

Mar. 10, 1997 (JP) .................................................... 9-054612

(51) Int. Cl.[7] .................................................... G01N 15/02
(52) U.S. Cl. .............................. 356/335; 356/436; 377/11
(58) Field of Search ...................... 356/335, 336, 356/338, 342, 442, 440, 432, 434; 250/574, 575, 573; 377/11, 10

(56) References Cited

U.S. PATENT DOCUMENTS

| | | | |
|---|---|---|---|
| 3,879,129 | * 4/1975 | Inoue | 356/442 |
| 3,880,526 | * 4/1975 | Kobayashi et al. | 356/442 |
| 4,072,421 | * 2/1978 | Coyne et al. | 356/442 |
| 4,198,161 | 4/1980 | Larson . | |
| 4,637,719 | * 1/1987 | Herman | 356/442 |
| 4,752,131 | 6/1988 | Eisenlauer et al. . | |
| 4,906,101 | * 3/1990 | Lin et al. | 356/442 |
| 4,940,326 | 7/1990 | Tatsuno . | |
| 5,257,087 | 10/1993 | Furuya . | |
| 5,619,333 | * 4/1997 | Staff et al. | 356/436 |

FOREIGN PATENT DOCUMENTS

| | | |
|---|---|---|
| 0324413 | 7/1989 | (EP) . |
| 0350768 | 1/1990 | (EP) . |
| 2016407 | 7/1994 | (RU) . |

OTHER PUBLICATIONS

Colloid & Polymer Sci., vol. 258, 1980, pp. 1303–1304, XP002066789.
Journal of Colloid and Interface Science, vol. 105, No. 2, Jun. 1985, "Turbidity Fluctuations in Flowing Suspensions", John Gregory.

* cited by examiner

*Primary Examiner*—Hoa Q. Pham
(74) *Attorney, Agent, or Firm*—Pearne & Gordon LLP

(57) ABSTRACT

A method of measuring turbidity includes irradiating specimen water with a light beam, using photoelectric conversion means for subjecting to photoelectric conversion the light scattered by fine particles in the specimen water, inputting a pulse signal as an input signal 7 obtainable from the photoelectric conversion whenever the fine particle passes through the light beam so as to measure its peak value in a peak holding circuit 13, obtaining the number concentration of fine particles in the specimen water on the basis of particle diameter divisions according to the measured value, and multiplying the number concentration by an individual coefficient on the basis of the particle diameter divisions in order to obtain the turbidity of the specimen water.

14 Claims, 3 Drawing Sheets

METHOD AND APPARATUS FOR MEASURING TURBIDITY

BACKGROUND OF THE INVENTION

1. Field of the Invention

The present invention relates to a method and apparatus for measuring turbidity.

2. Description of the Related Art

A turbidity meter is used for measuring the turbidity of raw and purified water in water treatment in which a transmitted light, a scattered light, a surface scattering light, and a transmitted—scattered light system are employed.

In the transmitted light system, there follows such a method that when specimen water flowing through a flow cell is irradiated with a light beam from a light source, the light transmitted through the fluid is received by a photoelectric converter, and the voltage converted therein is reconverted into turbidity. This system is fit for examining specimen water having high turbidity.

In the scattered light system, there follows such a method that when specimen water flowing through a flow cell is irradiated with a light beam from a light source, the light scattered by fine particles within the fluid in received by a photoelectric converter, and the voltage converted therein is reconverted into turbidity. This system is fit for examining specimen water having low turbidity.

In the surface scattering light system, there follows such a method that when the surface of specimen water is not irradiated via a flow cell but directly irradiated with a light beam from a light source, the light scattered by fine particles in the proximity of the surface of the specimen water is received by a photoelectric converter, and the voltage converted therein is reconverted into turbidity. This system features that the specimen water remains unaffected by the contamination of the flow cell because the flow cell and the specimen water are not brought into contact with each other in the light beam irradiation area.

In the transmitted—scattered light system, a quantity resulting from dividing scattered light intensity by transmitted light intensity is reconverted into turbidity. This system allows measurement of from low turbidity up to high turbidity.

Close control over purified water quality is increasingly exercised in order to cope with cryptospolydium and the like, and according to the tentative guiding principle announced by the Ministry of Welfare reads "Turbidity shall be maintained at 0.1 or lower at the exit of a filter reservoir of any purification plant where raw water for city water may be contaminated by cryptospolydium." As a result, an on-line turbidity meter capable of stably measuring a turbidity of 0.1 or lower becomes essential. However, it is difficult for a typical conventional turbidity meter to measure such a low turbidity because the conventional turbidity meter is designed to catch the scattering and transmittance of a light beam due to fine particles in the form of groups as the number of fine particles within an observation area considerably small. In order to make the aforementioned measurement possible, the probability of the presence of fine particles has to be increased by modifying the conventional turbidity meter in that the optical path length is increased in the transmitted light system and otherwise the light beam irradiation area is enlarged in the scattered light system. However, since the aforementioned modification results in enlarging the optical system of the turbidity meter, attaining two-digit high sensitivity in the turbidity measurement is hardly possible when size restriction is taken into consideration.

Further, membrane treatment technology is beginning to be employed in the water treatment and in order to secure the stability of treated water obtained from the membrane treatment, a turbidity meter and a fine particle counter are used for monitoring the treated water. However, the conventional turbidity meter is usable for detecting only a case where the rupture of membranes causes a considerable quantity of raw water to flow into the treated water, and is unable to detect the outflow of a small quantity of raw water when some membranes are cracked; the indicated value of turbidity at this time is almost zero like the water subjected to normal membrane treatment. It is therefore difficult to discover the abnormal condition of treated water through turbidity measurement in its early stages. On the other hand, the fine particle counter is used for measuring the number concentration of fine particles having a particle diameter greater than a nominal pore diameter of the membrane in water treatment so as to monitor an increase in fine particles when the membrane is ruptured or cracked. As the number concentration of fine particles is obtained by counting the optical pulses scattered or intercepted by the respective fine particles one by one, sensitivity is good in comparison with turbidity in a region where the probability of the presence of fine particles in the observation area is low, so that the fine particle counter is fit for detecting the abnormal condition of the membrane. However, care should be taken to observe an error in miscounting the number of fine particles when the probability of presence of fine particles in the observation area increases.

In the case of measurement in an extremely low turbidity region, that is, in a case where treated water and membrane treated water at a turbidity of 0.1 or lower, the sensitivity of the conventional turbidity meter is insufficient and it is consequently preferred to use the fine particle counter for measuring the number concentration of fine particles within treated water. However, there is a history that turbidity has been measured for many years in the field of water treatment, and there is no experience that water quality is determined on the basis of a value of the number concentration of fine particles which is measured in a purification plant or the like.

SUMMARY OF THE INVENTION

The present invention has been made in view of the above circumstances, and therefore an object of the present invention is to provide a method and apparatus effective for converting the number concentration of measurable fine particles into turbidity and outputting the turbidity thus converted even in a low turbidity region where turbidity measurement is impossible.

In order to accomplish the object above, according to a first aspect of the invention, there is provided a method of measuring turbidity comprising the steps of irradiating specimen water with a light beam, using photoelectric conversion means for subjecting to photoelectric conversion the light scattered by fine particles in the specimen water, obtaining the number concentration of fine particles in the specimen water on the basis of particle diameter divisions according to each pulse signal in a unit period which is obtainable by the photoelectric conversion whenever the fine particle passes through the light beam, and multiplying the number concentration by an individual coefficient on the basis of the particle diameter divisions in order to obtain the turbidity of the specimen water.

According to a second aspect of the invention, there is provided a method of measuring turbidity comprising the steps of irradiating specimen water with a light beam, using photoelectric conversion means for subjecting to photoelectric conversion the light transmitted through fine particles in the specimen water, obtaining the number concentration of fine particles in the specimen water on the basis of particle diameter divisions according to a pulse signal obtainable by the photoelectric conversion whenever the fine particle intercepts the light beam, and multiplying the number concentration by an individual coefficient on the basis of the particle diameter divisions in order to obtain the turbidity of the specimen water.

According to a third aspect of the present invention, the individual coefficient is a light scattering sectional area obtained on the basis of an average value in each particle diameter division, the wavelength of the light beam, and the refractive indexes of the specimen water and the fine particle.

According to a fourth aspect of the present invention there is provided a method of measuring turbidity comprising the steps of irradiating specimen water with a light beam, using photoelectric conversion means for subjecting to photoelectric conversion the light scattered by fine particles in the specimen water, adding a peak value of each pulse signal in a unit period which is obtainable by the photoelectric conversion whenever the fine particle passes through the light beam, and multiplying the added value by a coefficient in order to obtain the turbidity of the specimen water.

According to a fifth aspect of the invention, there is provided a method of measuring turbidity comprising the steps of irradiating specimen water with a light beam, using photoelectric conversion means for subjecting to photoelectric conversion the light transmitted through fine particles in the specimen water, adding a peak value of each pulse signal in a unit period which is obtainable from the photoelectric conversion whenever the fine particle passes through the light beam, and multiplying the added value by a coefficient in order to obtain the turbidity of the specimen water.

According to a sixth aspect of the present invention, the coefficient is obtained on the basis of a value resulting from dividing the sectional area of the light beam by the flow rate of the specimen water at the time of addition and the light beam intensity.

According to a seventh aspect of the invention, there is provided an apparatus for measuring turbidity, comprising a light source for irradiating specimen water with a light beam, photoelectric conversion means for subjecting to photoelectric conversion the light scattered by fine particles within the specimen water passed through the light beam irradiation area, and arithmetic means for obtaining the number concentration of fine particles in the specimen water on the basis of particle diameter divisions according to a pulse signal obtainable by the photoelectric conversion whenever the fine particle passes through the light beam, and multiplying the number concentration by an individual coefficient on the basis of the particle diameter divisions in order to obtain the turbidity of the specimen water.

According to an eighth aspect of the invention, there is provided an apparatus for measuring turbidity, comprising a light source for irradiating specimen water with a light beam, photoelectric conversion means for subjecting to photoelectric conversion the light transmitted through the specimen water passed through the light beam irradiation area, and arithmetic means for obtaining the number concentration of fine particles in the specimen water on the basis of particle diameter divisions according to a pulse signal obtainable by the photoelectric conversion whenever the fine particle intercepts the light beam, and multiplying the number concentration by an individual coefficient on the basis of the particle diameter divisions in order to obtain the turbidity of the specimen water.

According to a ninth aspect of the invention, the individual coefficient is a light scattering sectional area obtained on the basis of an average value in each particle diameter division, the wavelength of the light beam, and the refractive indexes of the specimen water and the fine particle.

According to a tenth aspect of the invention, there is provided an apparatus for measuring turbidity, comprising a light source for irradiating specimen water with a light beam, photoelectric conversion means for subjecting to photoelectric conversion the light scattered by fine particles within the specimen water passed through the light beam irradiation area, and arithmetic means for adding a peak value of a pulse signal in a unit period which is obtainable by the photoelectric conversion whenever the fine particle passes through the light beam, and multiplying the added value by a coefficient in order to obtain the turbidity of the specimen water.

According to an eleventh aspect of the present invention, there is provided an apparatus for measuring turbidity, comprising a light source for irradiating specimen water with a light beam, photoelectric conversion means for subjecting to photoelectric conversion the light transmitted through the specimen water passed through the light beam irradiation area, and arithmetic means for adding a peak value of a pulse signal in a unit period which is obtainable by the photoelectric conversion whenever the fine particle intercepts the light beam, and multiplying the added value by a coefficient in order to obtain the turbidity of the specimen water.

According to a twelfth aspect of the present invention, the coefficient is obtained on the basis of a value resulting from dividing the sectional area of the light beam by the flow rate of the specimen water at the time of addition and the light beam intensity.

According to a thirteenth aspect of the invention, the arithmetic means obtains the turbidity on the basis of a measured value from a peak holding circuit for measuring a peak value of a pulse signal from the photoelectric conversion means.

According to a fourteenth aspect of the invention, the arithmetic means obtains the turbidity on the basis of comparison outputs from a plurality of comparators for comparing the peak value of a pulse signal from the photoelectric conversion means with each of the different threshold values.

DETAILED DESCRIPTION OF THE PREFERRED EMBODIMENT

Referring to the accompanying drawings, there is given a detailed description of embodiments of the present invention.

(Embodiment 1)

Figure 1:
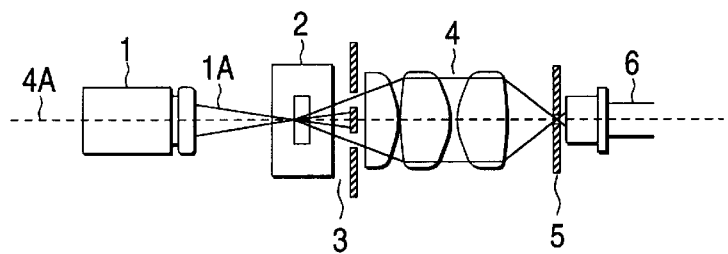
FIG. 1 is a diagram illustrating an optical system configuration in an apparatus according to the present invention.
Figure 2:
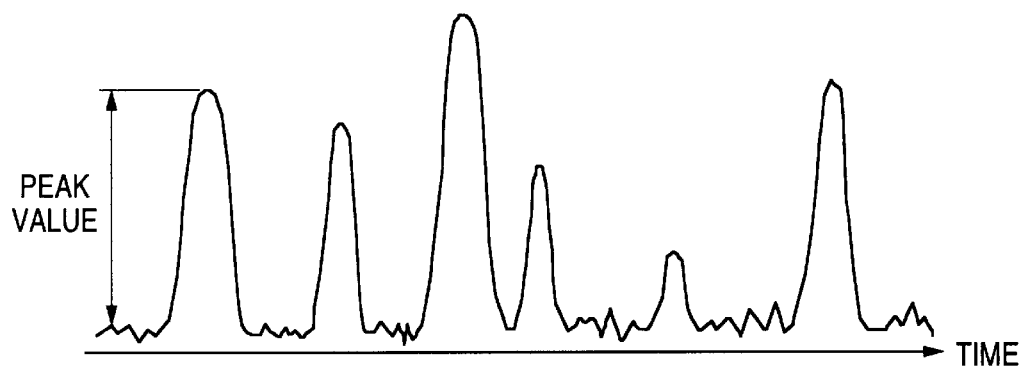
FIG. 2 is a chart showing the relation between a pulse signal and a peak value of the pulse due to fine particles.
Figure 3:
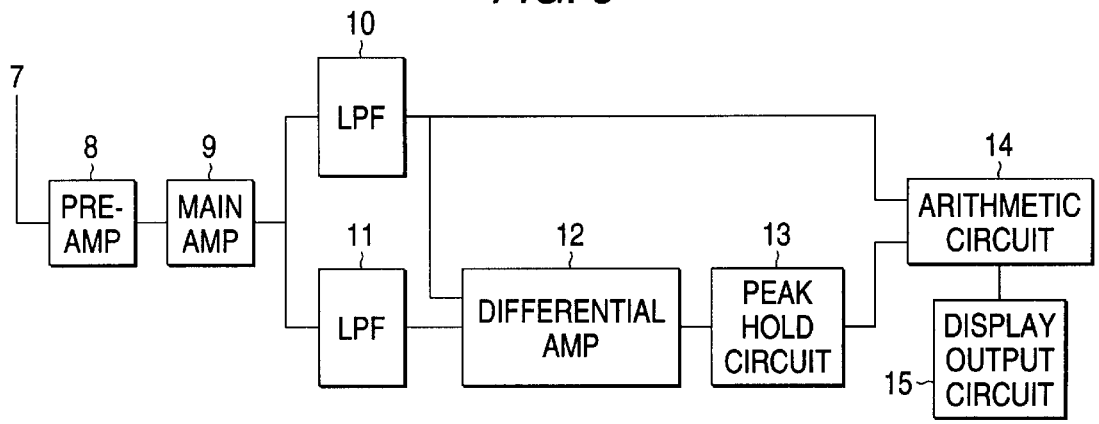
FIG. 3 is a block diagram illustrating an electronic circuit system (using a peak holding circuit) in the apparatus according to the present invention.

FIG. 1 shows an optical system for common use in apparatus embodying the present invention intended for measuring turbidity with a front scattered light system adopted therein. In FIG. 1, a light beam 1A irradiated from a light source 1 is scattered by fine particles existing in specimen water passing through a light beam irradiation area 15 of a flow cell 2. The light directly emitted from the light source 1 and passed through the specimen water and the flow cell 2 is intercepted by a beam stop 3 installed on the rear side of the flow cell 2 as viewed from the light source 1, and part of the light scattered by the fine particles and passed through holes bored in the beam stop 3 is condensed by a condenser lens 4 installed on the same axis as the optical axis 4A of the light beam. The scattered light is passed through a pin hole 5 provided for blocking off stray light before being converted into an electric signal by a photoelectric conversion element 6 installed on the same axis as the optical axis 4A of the light beam. The electric signal is detected as a pulse having a peak value corresponding to the size of the fine particle every time the fine particle passes through the light beam irradiation area as shown in FIG. 2. The electric signal thus detected is input to an electronic circuit of FIG. 3 as an input signal and amplified in a preamplifier 8 and a main amplifier 9 and then noise is removed in a low-pass filter (hereinafter called LPF) 11. On the other hand, the average value of the electric signal, that is, a direct current component due to the stray light is obtained by smoothing the electric signal that is output from the main amplifier 9 by means of a LPF 10 where the cutoff frequency is sufficiently low.

Subsequently, the average value of the electric signal obtained by the LPF 10 is subtracted from the electric signal passed through the LPF 11 in a differential amplifier 12, whereby an electric signal resulting from the subtraction of the direct current component due to the stray light is obtained. Then the peak value of the pulse signal generated in the electric signal is measured in a peak holding circuit 13. When the flow rate of the specimen water ranges from 10 to 100 ml/min, for example, the cutoff frequency of the LPF 10 and that of the LPF 11 are preferably 30 Hz or lower and 100 KHz or higher, respectively. The peak value measured by the peak holding circuit 13 whenever the fine particles pass through the light irradiation area, thus causing the pulse signal to be generated, is compared with a threshold value division corresponding to a particle diameter division which is predetermined by an arithmetic circuit 14 and counted on the basis of the particle diameter divisions. A value resulting from converting the number counted for each division to the number counted per unit time after the passage of sampling time is multiplied by a coefficient and then divided by a sampling flow rate in order to obtain the number concentration of fine particles on the basis of the particle diameter divisions. Further, turbidity is made obtainable by multiplying different light scattering sectional areas on the basis of the particle diameter divisions, and the turbidity or the number concentration of fine particles on the basis of the particle diameter divisions can be displayed.output from a display.output circuit 15.

The contents of the aforementioned measurement of turbidity will subsequently be described with reference to numerical formulas.

Assuming that the particle diameter d of a fine particle in specimen water is constant, that is, in the case of monodispersion, turbidity D1 is displayed by using the number n1 of fine particles per cubic volume and the light scattering sectional area C1 of the fine particle as follows:

$$D1 = n1 \, C1 \quad (1)$$

Therefore, turbidity in obtainable from multiplying the number of pulse signals observed in the apparatus according to the present invention and proportional to the number of fine particles by the light scattering sectional area. Since the light scattering sectional area is the quantity varied with the particle diameter, it is usable for measuring mono-dispersed specimen water; in other words, the Eq. (1) is not applicable to ordinary specimen water because actual specimen water is not a mono-dispersed one. Consequently, the number concentration of fine particles on the basis of the particle diameter divisions has to be multiplied by the individual scattering sectional area on the basis of the particle diameter divisions in order to obtain turbidity D from the sum as shown by Eq. (2).

$$D = {}_d\Sigma n_d C_d \quad (2)$$

Figure 4:
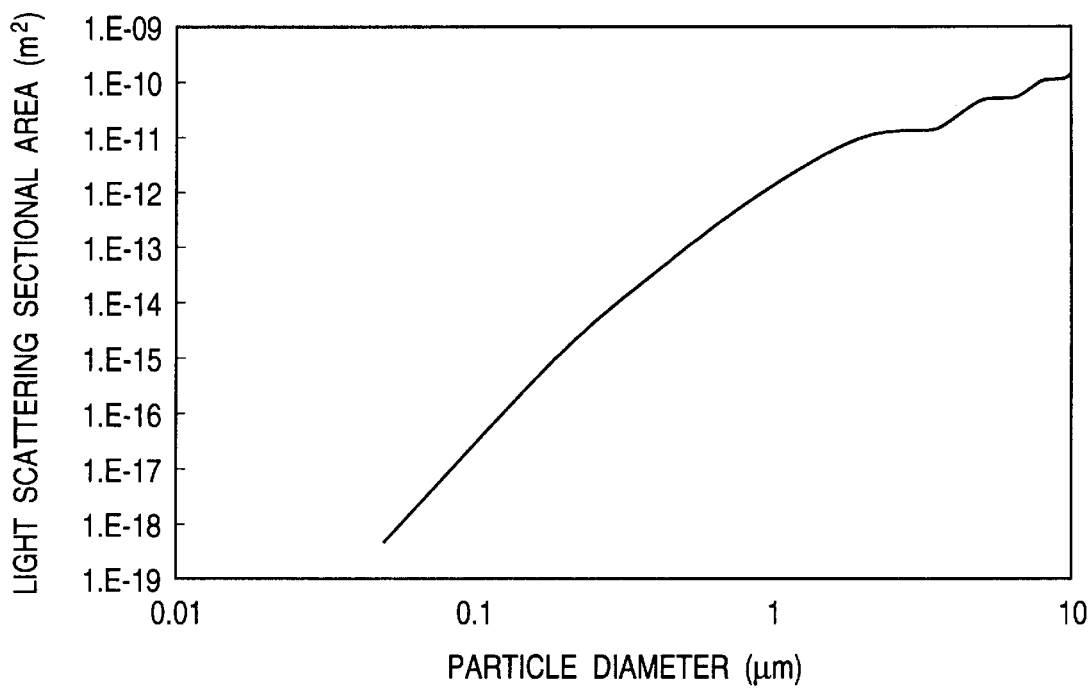
FIG. 4 is a graph showing the relation between particle diameters and light scattering sectional areas.

$C_d$ represents a light scattering sectional area in the particle diameter division d of fine particles, which is obtainable from the simulation based on the light scattering logic of Mie. The light scattering logic of Mie is a logic that the scattered light intensity relating to all the spherical particles which are subjected to Rayleigh scattering which is caused by fine particles smaller than the wavelength, the scattering of Mie which is caused by fine particles as large as the wavelength and the Fraunhofer's diffraction which is caused by fine particles larger than the wavelength is obtained as a complete solution of the Maxwell's electromagnetic equations. Specifically, a light scattering sectional area proportional to the scattered light intensity which is integrated with a predetermined light receiving region is calculated on the basis of the wavelength of an irradiated light, the refractive index of specimen water, the refractive index of fine particles and the radius of fine particles. FIG. 4 shows a relation between the particle diameter and the light scattering sectional area with respect to fine particles made of a material 1.595 in refractive index in water (refractive index is 1.33) under the condition where the wavelength of the light source is 780 nm, which is obtained through the above calculation. Although $n_d$ represents the number of fine particles in the particle diameter division d per unit cubic volume, the use of the number $N_d$ of fine particles and a sampling flow rate F measured by the apparatus according to the present invention per unit time permits Eq. (2) to be expressed as follows:

$$D = {}_d\Sigma N_d C_d / F \quad (3)$$

If the particle diameter division is set to range from (1) 0.5 to 1 $\mu$m; (2) from 1 to 2 $\mu$m; and (3) 2 $\mu$m or greater, Eq. (3) is expressed by $$D = (N1C1 + N2C2 + N3C3)/F \quad (4)$$

In this case, N1–N3 represent the number of fine particles per unit time in the particle diameter divisions (1)–(3), whereas C1–C3 represent average values of light scattering sectional areas in the respective particle diameter divisions obtained from the light scattering simulation; namely, C1=5.32×10$^{-13}$, C2=5.36×10$^{-12}$, C3=5.18×10$^{-11}$.

Figure 5:
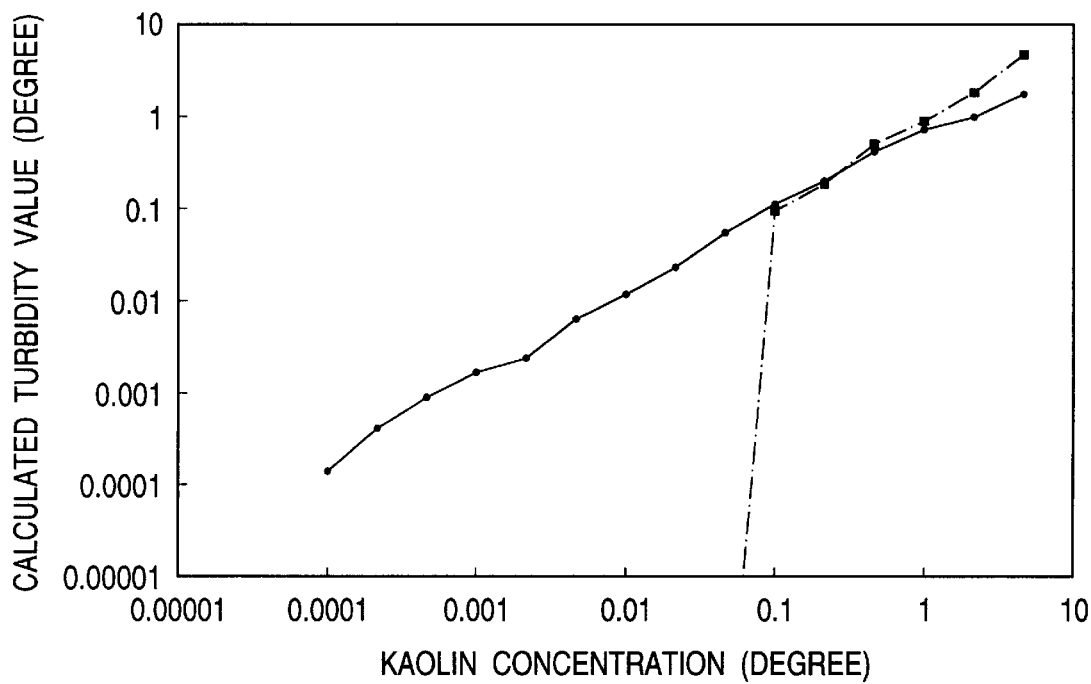
FIG. 5 is a graph showing the relation between kaolin concentration and calculated turbidity values.

FIG. 5 shows calculated turbidity values resulting from letting specimen water actually flow at 50 ml/min through the apparatus according to the present invention, proving that this apparatus is capable of calculating turbidity with a sensitivity of 1,000 times greater than before even at the time of low turbidity when the measured value is 0 by the use of a turbidity meter of the transmitted—scattered light system applied to the specimen water.

In the presence of many light-absorbing particles out of the fine particles contained in specimen water, it is more accurate to obtain turbidity by multiplying the number concentration of fine particles on the basis of the particle diameter divisions by an attenuating sectional area resulting from adding the light scattering sectional area and an absorbing sectional area than to obtain turbidity by multiplying the number concentration of fine particles on the basis of the particle diameter divisions by the light scattering sectional area obtainable from the light scattering simulation.

Although turbidity has been obtained by multiplying the number concentration of fine particles on the basis of the particle diameter divisions by the light scattering sectional area according to this embodiment of the present invention, it may be preferred to obtain turbidity by obtaining a quantity (a turbidity conversion coefficient) contributing to the turbidity of one fine particle on the basis of the particle diameter division from experiments and multiplying the number concentration of fine particles on the basis of the particle diameter divisions by the value of the quantity thus obtained in order to add up the values.

In the arithmetic circuit 14, the output of the LPF 10 is observed and when the output exceeds a predetermined upper limit value, it is detected that the contamination of the flow cell 2 is in such a state that it impedes the measurement, whereas when the output becomes lower than a predetermined lower limit value, the light beam has not been irradiated from the light source 1 any longer, that is, the abnormal state of the light source 1 is detected. Then each of the outputs detected is supplied to the displaya.output circuit 15 and displayed to the effect.

(Embodiment 2)

Figure 6:
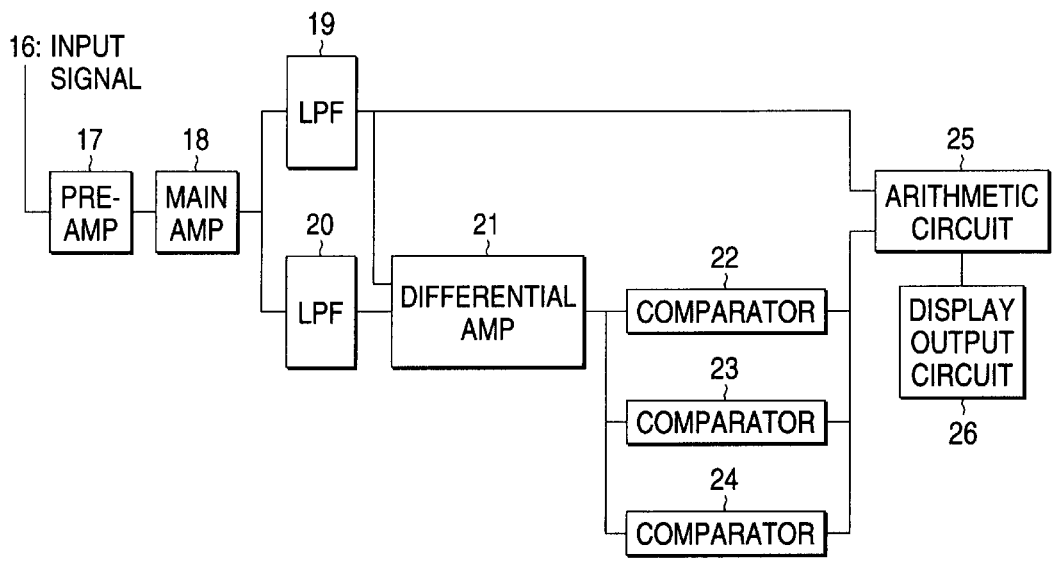
FIG. 6 is a block diagram illustrating an electronic circuit system (using comparators) in the apparatus according to the present invention.

Although the peak holding circuit has been used to detect the pulse peak value so as to measure the number concentration of fine particles on the basis of the particle diameter divisions in Embodiment 1 of the present invention, if the number of particle diameter divisions is small, comparators are prepared as many as the number of particle diameter divisions instead of the peak holding circuit as shown in FIG. 6 in order that number concentration of fine particles may be measured on the basis of the particle diameter divisions by providing threshold values corresponding to the respective particle diameter divisions. A description will be given of turbidity measurement when three particle diameter divisions are set up as in Embodiment 1 of the present invention; namely, (1) 0.5 to 1 μm; (2) from 1 to 2 μm; and (3) 2 μm or greater.

Figure 7:
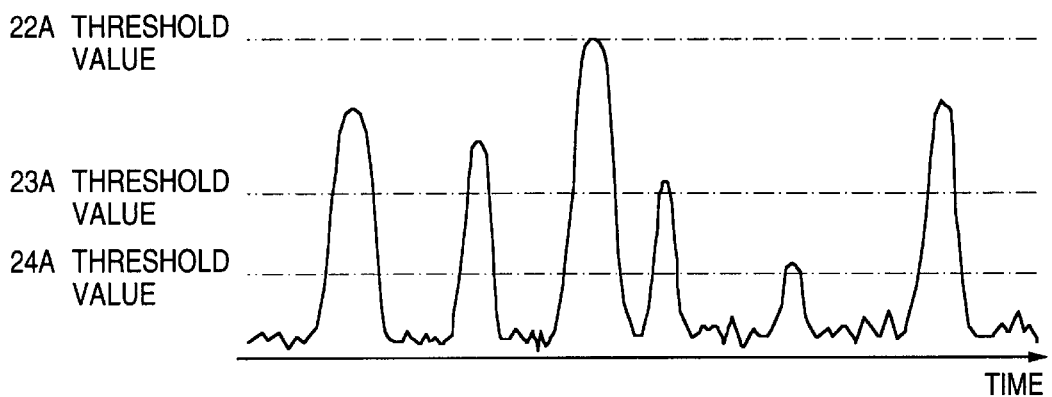
FIG. 7 is a chart showing the relation between a pulse signal due to fine particles and threshold values of comparators.

A pulse signal having a peak value corresponding to the size of the fine particle every time the fine particle passes through a light beam irradiation area is, as in Embodiment 1 of the present invention, input to an electronic circuit of FIG. 6 as an input signal 16 from a photoelectric conversion element 6. The input signal is amplified in a preamplifier 17 and a main amplifier 18 and then noise is removed in a low-pass filter (hereinafter called LPF) 20. Subsequently, the average value of the electric signal obtained from the electric signal passed through the LPF 20 by smoothing the electric signal in a LPF 19 is subtracted in an differential amplifier 21, whereby an electric signal resulting from subtracting a direct current component due to stray light is input to comparators 22–24. The threshold values 22A–24A of the comparators are set at voltages corresponding to the respective particle diameter divisions as shown in FIG. 7, and the pulse signal is reduced to a binary value. Further, the number concentration of fine particles on the basis of the particle diameter divisions can be measured as in Embodiment 1 of the present invention by counting pulses having peak values not less than the threshold values corresponding to the respective particle diameter divisions. The values are then calculated as in Embodiment 1 of the present invention to obtain turbidity, and the turbidity or the number concentration of fine particles on the basis of the particle diameter divisions can be displayede.output by a display.output circuit 26.

(Embodiment 3)

Although turbidity has been obtained by measuring the number concentration of fine particles on the basis of the particle diameter divisions in Embodiments 1 and 2, turbidity may be obtained by the following method.

As in Embodiment 1, pulse signals due to fine particles are subjected to peak holding and the peak values of the respective pulses in a unit period are added up by the arithmetic circuit. Then, an added value of the peak values is multiplied by a coefficient. When the number concentration of fine particles for each of the particle diameter divisions is simultaneously measured, the peak values subjected to the peak holding are stored in the unit period as they are, and the added value of the peak values stored is multiplied by a coefficient. Consequently, the value thus obtained indicates turbidity and even specimen water different in particle size distribution is correlated with prior turbidity. When number concentration of fine particles is measured, the threshold divisions equivalent to the predetermined particle diameter divisions are compared with the prestored peak values and counted on the basis of the particle diameter divisions.

The contents of the aforementioned measurement of turbidity will subsequently be expressed by numerical formulas.

The pulse peak value $V_d$ due to a fine particle having a particle diameter d observed in the apparatus according to the present invention is a value proportional to $C_d$ as shown by Eq. (5).

$$V_d = I_o W R A_v C_d / S \tag{5}$$

where Io=light beam intensity; W=light receiving sensitivity of a photoelectric conversion element in the wavelength band of a light source; R=load resistance value for converting the signal subjected to photoelectric conversion to a voltage signal; $A_v$=amplification factor of a circuit including a preamplifier and a main amplifier; and S=sectional area of the light beam in an observation area. Therefore, though the number concentration of fine particles observed on the basis of the particle diameter divisions has been multiplied collectively by the light scattering sectional area corresponding to the particle diameter division according to Eq. (3) in Embodiment 1, turbidity may also be obtained by adding up the peak values of the pulses measured within unit time as in this embodiment of the present invention. In other words, assuming N pulses are observed within unit time, $$D = \sum_{i=1}^{N} (ViS)/(FIo\, WRA_v) \qquad (6)$$

the turbidity can be expressed from Eqs. (3) and (5).

In Eq. (6), in order to replace the total of the pulse peak values for each of the particle diameter divisions by a time series total, d and $(N_d V_d)$ in Eq. (3) are replaced by i and Vi, respectively. Since W, R and $A_v$ are circuit constants, the above coefficient by which the added value of the peak values is multiplied is S/(FIo).

The method according to this embodiment of the present invention is equivalent to a method in which a number of particle diameter divisions are provided as described in Embodiments 1 and 2, and features that highly accurate turbidity measurement is accomplished. When turbidity and the number concentration of fine particles on the basis of the particle diameter divisions are simultaneously measured, however, it is needed to store the peak value of the individual pulse as this requires an extra memory capacity. Consequently, there are cases where the adoption of the method described in Embodiment 1 or 2 is preferred.

Although the pulse peak value of each fine particle is multiplied by the sectional area of the light beam and the result is divided by the sampling flow rate and the light beam intensity to obtain turbidity according to this embodiment of the present invention, it may be preferred to measure a standard turbidity fluid beforehand in order to determine a coefficient by which the pulse peak value of each fine particle is multiplied.

Although the front scattered light system has been employed as the optical system in Embodiments 1–3 of the present invention, a side scattered light system or a combination of front and side scattered light systems, a light intercepting system or the like may be employed and as long as any other system has the function of outputting the number concentration of fine particles on the basis of the particle diameter divisions, conversion to turbidity is readily accomplishable. In the case of a light intercepting system, for example, a stop having holes for letting only the light beam 1A passes therethrough (i.e., intercepting the scattered light) is installed in place of the beam stop 3; the light passed through the holes of the stop is subjected by the photoelectric conversion element 6 to photoelectric conversion via the pin hole 5; and the output can be processed likewise with the arrangements of FIGS. 3 and 6.

As the present invention necessitates making measurement upon such conditions as the uniform distribution of intensity within the beam, a method of using a flat beam as disclosed in Japanese Patent Laid-Open No. 6246/1990 or a method of scanning a beam as disclosed in Japanese Patent Laid-Open No. 288139/1986 is already well known as what is capable of fulfilling the above conditions.

According to the present invention, the quantity of contribution to turbidity that one fine particle has is added up on the basis of fine particles, whereby turbidity measurement in a low turbidity region that the conventional turbidity meter is hardly able to deal with is made achievable. Even when specimen water different in particle size distribution is examined, turbidity measurement correlated with prior turbidity is made possible. Thus, the present invention is applicable to not only the maintenance and control of water quality at the exit of a filter reservoir but also the abnormality detection sensor of a membrane module in a membrane treatment system.

What is claimed is:

1. A method of measuring turbidity, comprising the steps of:

irradiating specimen water with a light beam;

subjecting to photoelectric conversion the light scattered by fine particles in the specimen water by using photoelectric conversion means;

obtaining the number concentration of fine particles in the specimen water on the basis of particle diameter divisions according to a pulse signal obtainable from the photoelectric conversion each time individual fine particles pass through the light beam; and multiplying the number concentration by an individual coefficient on the basis of the particle diameter divisions in order to obtain the turbidity of the specimen water.

2. A method of measuring turbidity, comprising the steps of:

irradiating specimen water with a light beam;

subjecting to photoelectric conversion the light transmitted through the specimen water by using photoelectric conversion means;

obtaining the number concentration of fine particles in the specimen water on the basis of particle diameter divisions according to a pulse signal obtainable from the photoelectric conversion each time individual fine particles pass through the light beam; and multiplying the number concentration by an individual coefficient on the basis of the particle diameter divisions in order to obtain the turbidity of the specimen water.

3. A method of measuring turbidity as claimed in claim 1 or claim 2, wherein the individual coefficient is a light scattering sectional area obtained on the basis of an average value of the particle diameters in each particle diameter division, the wavelength of the light beam, and the refractive indexes of the specimen water and the fine particle.

4. A method of measuring turbidity, comprising:

the steps of irradiating specimen water with a light beam;

subjecting to photoelectric conversion the light scattered by fine particles in the specimen water by using photoelectric conversion means; and adding the peak value of each pulse signal in a unit period which is obtainable by the photoelectric conversion whenever the fine particle pauses through the light beam, and multiplying the added value by a coefficient in order to obtain the turbidity of the specimen water.

5. A method of measuring turbidity, comprising the steps of:

irradiating specimen water with a light beam;

subjecting to photoelectric conversion the light transmitted through the specimen water by using photoelectric conversion means;

adding the peak value of each pulse signal in a unit period which is obtainable by the photoelectric conversion whenever the fine particle passes through the light beam; and multiplying the added value by a coefficient in order to obtain the turbidity of the specimen water.

6. A method of measuring turbidity as claimed in claim 4 or 5, wherein the coefficient is obtained on the basis of a value resulting from dividing the sectional area of the light beam by the flow rate of the specimen water at the time of addition and the light beam intensity.

7. An apparatus for measuring turbidity comprising:

a light source for irradiating specimen water with a light beam;

photoelectric conversion means for subjecting to photoelectric conversion the light scattered by fine particles within the specimen water passed through the light beam irradiation area; and arithmetic means for obtaining the number concentration of fine particles in the specimen water on the basis of particle diameter divisions according to a pulse signal obtainable from the photoelectric conversion each time individual fine particles pass thorough the light beam, and multiplying the number concentration by an individual coefficient on the basis of the particle diameter divisions in order to obtain the turbidity of the specimen water.

8. An apparatus for measuring turbidity, comprising:

a light source for irradiating specimen water with a light beam;

photoelectric conversion means for subjecting to photoelectric conversion the light transmitted through the specimen water passed through the light beam irradiation area; and arithmetic means for obtaining the number concentration of fine particles in the specimen water on the basis of particle diameter divisions according to a pulse signal obtainable from the photoelectric conversion each time individual fine particles intercept the light beam, and multiplying the number concentration by an individual coefficient on the basis of the particle diameter divisions in order to obtain the turbidity of the specimen water.

9. An apparatus for measuring turbidity as claimed in claim 7 or 8, wherein the individual coefficient is a light scattering sectional area obtained on the basis of an average value of the particle diameters in each particle diameter division, the wavelength of the light beam, and the refractive indexes of the specimen water and the fine particle.

10. An apparatus for measuring turbidity, comprising:

a light source for irradiating specimen water with a light beam;

photoelectric conversion means for subjecting to photoelectric conversion the light scattered by fine particles within the specimen water passed through the light beam irradiation area; and arithmetic means for adding the peak value of a pulse signal in a unit period which is obtainable by the photoelectric conversion whenever the fine particle passes through the light beam, and multiplying the added value by a coefficient in order to obtain the turbidity of the specimen water.

11. An apparatus for measuring turbidity, comprising:

a light source for irradiating specimen water with a light beam;

photoelectric conversion means for subjecting to photoelectric conversion the light transmitted through the specimen water passed through the light beam irradiation area; and arithmetic means for adding the peak value of a pulse signal in a unit period which is obtainable by the photoelectric conversion whenever the fine particle intercepts the light beam, and multiplying the added value by a coefficient in order to obtain the turbidity of the specimen water.

12. An apparatus for measuring turbidity as claimed in either claim 10 or 11, wherein the coefficient is obtained on the basis of a value resulting from dividing the sectional area of the light beam by the flow rate of the specimen water at the time of addition and the light beam intensity.

13. An apparatus for measuring turbidity as claimed in one of claims 7, 8, 10 and 11, wherein the arithmetic means obtains the turbidity on the basis of a measured value from a peak holding circuit for measuring the peak value of a pulse signal from the photoelectric conversion means.

14. An apparatus for measuring turbidity as claimed in one of claims 7, 8, 10 and 11, wherein the arithmetic means obtains the turbidity on the basis of comparison outputs from a plurality of comparators for comparing the peak value of a pulse signal from the photoelectric conversion means with each of the different threshold values.

* * * * *